United States Patent [19]

George et al.

[11] Patent Number: 5,254,560
[45] Date of Patent: Oct. 19, 1993

[54] 2-PIPERIDINYLPYRIMIDINE-4-CARBOXAMIDE DERIVATIVES, AND THEIR USE IN THERAPEUTICS

[75] Inventors: Pascal George, St. Arnoult en Yvelines; Christian Maloizel, Meudon; Benoit Marabout, Massy; Jean-Pierre Merly, Sceaux, all of France

[73] Assignee: Synthelabo, Le Plessis Robinson, France

[21] Appl. No.: 904,061

[22] Filed: Jun. 26, 1992

[30] Foreign Application Priority Data

Jun. 27, 1991 [FR] France ................... 91 07938
May 18, 1992 [FR] France ................... 92 06004

[51] Int. Cl.$^5$ ............... C07D 401/04; A61K 31/505
[52] U.S. Cl. ...................................... 514/275; 544/332
[58] Field of Search ...................... 544/332; 514/275

[56] References Cited

U.S. PATENT DOCUMENTS 4,853,387  8/1989  Manoury et al. ................ 514/272

FOREIGN PATENT DOCUMENTS 0480794  4/1992  European Pat. Off. .

OTHER PUBLICATIONS

Chemical Abstracts, No. 70, (1969), Abst. No. 76976P, Mamaev et al.

Primary Examiner—John M. Ford
Attorney, Agent, or Firm—Jacobson, Price, Holman & Stern

[57] ABSTRACT

A compound which is a carboxamide derivative of general formula (I)

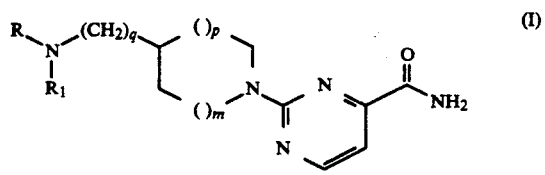

in which R represents a hydrogen atom, a methyl group or a phenoxyalkyl group of general formula

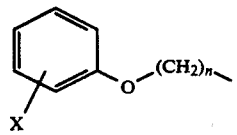

in which
X represents one or more substituents independently chosen from hydrogen, fluorine, chlorine, methyl, 1-methylethyl and methoxy and
n is 2 or 3,
m is 0 or 1 and
p is 1 or 2 such that m+p=2
q is 0 or 1, and
$R_1$ represents a hydrogen atom or a methyl group, or a pharmaceutically acceptable acid addition salt thereof. Process for their preparation and their therapeutic use.

8 Claims, No Drawings

2-PIPERIDINYLPYRIMIDINE-4-CARBOXAMIDE DERIVATIVES, AND THEIR USE IN THERAPEUTICS

The present invention relates to 2-piperidinylpyrimidine-4-carboxamide derivatives, to their preparation and to their therapeutic use.

SUMMARY OF THE INVENTION

The present invention provides compounds which are carboxamide derivatives of the general formula (I)

in which R represents a hydrogen atom, a methyl group or a phenoxyalkyl group of general formula in which
X represents one or more substituents independently chosen from hydrogen, fluorine, chlorine, methyl, 1-methylethyl and methoxy, and
n is 2 or 3,
m is 1,
p is 0 or 1, such that m+p=2
q is 0 or 1, and
$R_1$ represents a hydrogen atom or a methyl group pharmaceutically acceptable acid addition salts thereof.

The present invention also provides a process for the preparation of such compounds and to their therapeutic use.

The compounds of the invention thus exist in the form of a free base or of addition salts with acids. The compounds of the invention may be in the form of pure enantiomers or of mixtures of enantiomers, for example racemates.

DETAILED DESCRIPTION OF THE INVENTION

According to a preferred embodiment, R represents a hydrogen atom, a methyl group or a phenoxyalkyl group of general formula in which X represents one or more substituents independently chosen from fluorine, chlorine, methyl, 1-methylethyl and methoxy. In another embodiment R preferably represents a group of general formula in which X is as above, n is 2, m is 1, p is 1 and q is 0.

Preferably the pharmaceutically acceptable acid addition salt is the hydrochloride.

Examples of specific compounds of the invention are:

2-[4-[[2-(2-methoxyphenoxy)ethyl]amino]piperidin-1-yl]pyrimidine-4-carboxamide or the hydrochloride thereof;

2-(4-aminopiperidin-1-yl)pyrimidine-4-carboxamide or the hydrochloride thereof;

2-[4-[[3-(5-fluoro-2-methoxyphenoxy)propyl]amino]-piperidin-1-yl]pyrimidine-4-carboxamide or the hydrochloride thereof;

2-[4-[[[2-[5-methyl-2-(1-methylethyl)phenoxy]ethyl]amino]methyl]piperidin-1-yl]pyrimidine-4-carboxamide or the hydrochloride thereof;

2-[3-[[[2-(2-methoxyphenoxy)ethyl]amino]methyl]-piperidin-1-yl]pyrimidine-4-carboxamide or the hydrochloride thereof:

2-(4-aminopiperidin-1-yl)pyrimidine-4-carboxamide or the hydrochloride thereof;

2-[4-[[2-(5-fluoro-2-methoxyphenoxy)ethyl]amino]-piperidin-1-yl]pyrimidine-4-carboxamide or the hydrochloride thereof; and 2-[4-[[3-(4-fluorophenoxy)propyl]amino]piperidin-1-yl]pyrimidine-4-carboxamide or the hydrochloride thereof.

In accordance with the invention, the compounds of general formula (I) ca be prepared according to one of the processes illustrated by Schemes 1 and 2 which follow. The compounds of general formula (I) can be converted into acid addition salts in a manner know per se.

Scheme 1 concerns only the compounds of general formula (I) in which m=p=1 and q=0, which correspond to the general formula (I').

Scheme 1

-continued
Scheme 1

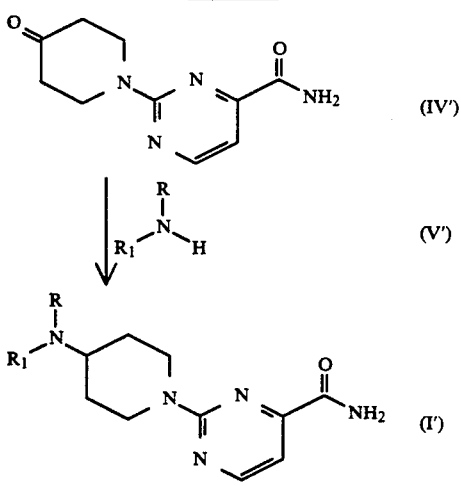

According to this scheme, the substituted piperidine of formula (II') is reacted with 2-chloropyrimidine-4-carboxamide of formula (III) in an aprotic solvent, for example acetonitrile, in the presence of an inorganic base, for example potassium carbonate. The acetal obtained in converted to ketone of formula (IV') by hydrolysis, for example with hydrochloric acid.

A derivative of general formula (I') is then obtained either in one stage, by reductive amination of the ketone of formula (IV') with an alkali metal cyanoborohydride, for example lithium cyanoborohydride, in an alcohol, for example methanol, in the presence of ammonium acetate, while maintaining the pH of the solution between 5 and 6;

or in two stages, by reaction of the ketone of formula (IV') with an amine of general formula (V'), in which R and $R_1$ are as defined above, in a solvent such as dichloromethane, in the presence of a dehydrating agent such as magnesium sulphate and then by reduction of the intermediate imine by an alkali metal hydride, for example sodium borohydride, in a solvent such as ethanol.

In a variation, a compound of general formula (I), in which R represents a phenoxyalkyl group as defined above, can be obtained from a compound of general formula (I) in which R represents hydrogen, as described below with regard to stage (V)→(I'') of Scheme 2.

The substituted piperidine of formula (II') or 1,4-dioxa-8-azaspiro[4.5]decane, is commercially available.

2-Chloropyrimidine-4-carboxamide of formula (III) can be prepared from 2-chloropyrimidine-4-carbonotrile by treatment with gaseous hydrochloric acid in formic acid, the said nitrile being itself prepared according to the method described in J. Het. Chem. 1964, 1, 130–133.

According to Scheme 2 below, a diamine of general formula (II), in which $R_1$, m, p and q are as defined above and R' represents an amine-protecting group, for example a benzyloxycarbonyl or a tert-butoxycarbonyl group, is first reacted with 2-chloropyrimidine-4-carboxamide of formula (III), in an aprotic solvent, for example N,N-dimethylformamide, in the presence of a base, for example an inorganic base, such as potassium carbonate, at a temperature of 20° to 40° C.

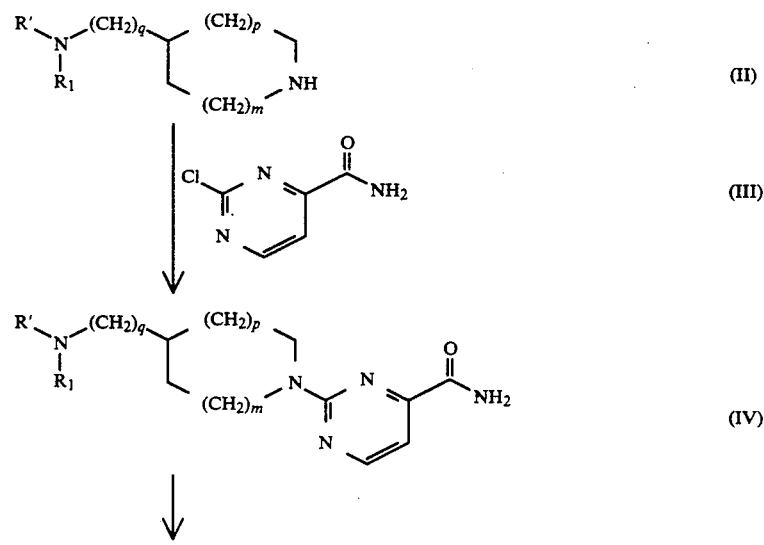

Scheme 2

Scheme 2

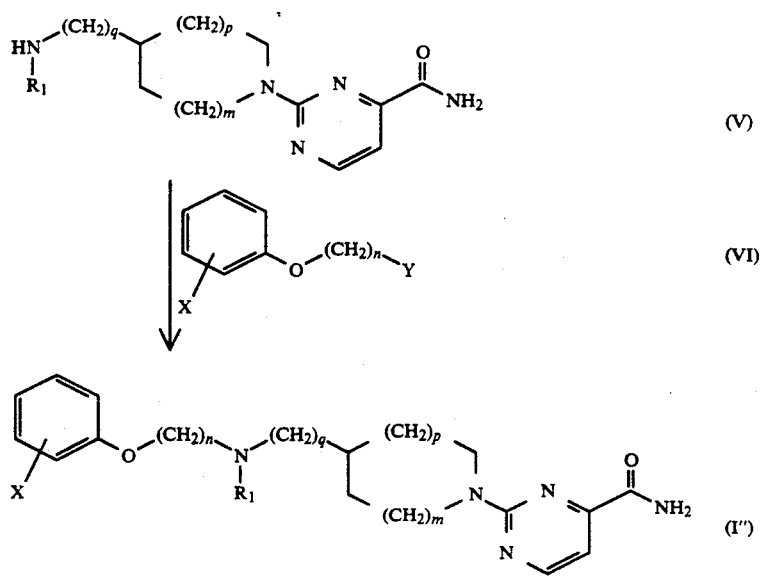

An aminopyrimidine of general formula (IV) is obtained which is then deprotected according to the nature of the protecting group R' by a method analogous to those described in the literature, for example by hydrogenation in the presence of palladium on charcoal (in the case of a benzyloxycarbonyl group) or by reaction with trifluoroacetic acid in dichloromethane (in the case of a tert-butoxycarbonyl group).

An aminopyrimidine of general formula (V) is obtained which corresponds to the general formula (I) when R represents hydrogen.

If necessary, it is finally reacted with a phenoxyalkyl halide of general formula (VI), in which X and n are as defined above and Y represents a chlorine or bromine atom, in an aprotic solvent, for example N,N-dimethylformamide, in the presence of a base, for example an inorganic base, such as potassium carbonate, at a temperature of 60° to 80° C.

The protected diamines of general formula (II), in which q represents the number 1, can be prepared by a method analogous to those described for the synthesis of tert-butyl piperidine-4-carbamate (q=0) in DE-A-2831431, EP-A-410278 and EP-A-417698.

2-Chloropyrimidine-4-carboxamide of formula (III) is described above with regard to Scheme 1.

The phenoxyalkyl halides of general formula (VI) can be prepared by methods analogous to those described in J. Pharm. Sci. 1984, 73/9, 1241–4, or in Synthesis 1990, 1069–71.

The following examples illustrate the preparation of some compounds according to the invention. The elemental microanalyses and the IR and NMR spectra confirm the structures of the products obtained. The compound numbers, given between parentheses in the headings of the examples, correspond to those in the Table given later.

EXAMPLE 1

Compound No. 3

2-[4-[[2-(2-Methoxyphenoxy)ethyl]amino]piperidin-1-yl]pyrimidine-4-carboxamide, hydrochloride

1.1. 2-(1,4-Dioxa-8-azaspiro[4.5]decan-8-yl pyrimidine-4-carboxamide 5 g (0.0318 mol) of 2-chloropyrimidine-4-carboxamide, 4.55 g (0.0318 mol) of 1,4-dioxa-8-azaspiro[4.5]decane and 6.6 g (0.0477 mol) of potassium carbonate are introduced into 100 ml of 2-butanone. The mixture is heated and stirred at reflux temperature for 6 hours. The mixture is filtered and the filtrate is concentrated under reduced pressure. 8.2 g of product are obtained which are recrystallised from 2-propanol. 4.1 g of product are obtained.

Melting point: 173°–175° C.

1.2. 2-(4-Oxopiperidin-1-yl)pyrimidine-4-carboxamide

A mixture of 4.1 g (0.0155 mol) of 2-(1,4-dioxa-8-azaspiro[4.5]decan-8-yl]pyrimidine-4-carboxamide, 41 ml of acetic acid and 4.1 ml of concentrated hydrochloric acid is heated at reflux temperature for 30 minutes. The mixture is concentrated under reduced pressure, the residue is then taken up in a mixture of dichloromethane and water, is alkalified with aqueous ammonia solution, extracted with dichloromethane, the organic phase is dried over magnesium sulphate, filtered and the solvent evaporated under reduced pressure. 3 g of compound are obtained.

Melting point: 208°–212° C.

1.3. 2-[4-[[2-(2-Methoxyphenoxy)ethyl]imino]piperidin-1-yl]pyrimidine-4-carboxamide 2.6 g (0.0118 mol) of 2-(4-oxopiperidin-yl)pyrimidine-4-carboxamide, 1.97 g (0.0188 mol) of 2-(2-methoxyphenoxy)ethylamine, 4.26 g (0.0354 mol) of magnesium sulphate and 152 ml of dichloromethane are introduced into a 500 ml flask and the mixture is stirred at room temperature for 24 hours.

The mixture is filtered, the precipitate is washed with dichloromethane and the filtrate is concentrated under reduced pressure. 4.35 g of oil are obtained, which is used as it is in the following stage.

1.4.
2-[4-[[2-(2-Methoxyphenoxy)ethyl]amino]piperidin-1-yl]pyrimidine-4-carboxamide, hydrochloride 4.35 g (0.0118 mol) of 2-[4-[[2-(2-methoxyphenoxy)ethyl]imino]piperidin-1-yl]pyrimidine-4-carboxamide are introduced into 150 ml of Methanol. The mixture is cooled in an ice bath, 1.35 g (0.0354 mol) of sodium borohydride are added and the mixture is stirred for 18 hours The mixture is concentrated and then taken up with a mixture of ethyl acetate and dilute hydrochloric acid, the aqueous phase is washed with ethyl acetate, then alkalified with aqueous ammonia and extracted with ethyl acetate. The organic phase is washed with water, dried over magnesium sulphate, filtered and concentrated under reduced pressure.

The base obtained is dissolved in 50 ml of 2-propanol and 50 ml of a 0.1 N hydrochloric acid solution in 2-propanol are added. The volume is concentrated by half and 1.2 g of compound which crystallises are obtained.
Melting point: 231°-233° C.

EXAMPLE 2

Compound No. 1

2-(4-Aminopiperidin-1-yl)pyrimidine-4-carboxamide, hydrochloride 1.1 g (0.005 mol) of 2-(4-oxopiperidin-1-yl)pyrimidine-4-carboxamide and 4.63 g (0.060 mol) of ammonium acetate are suspended in 15 ml of methanol. 0.24 g (0.005 mol) of lithium cyanoborohydride is added, the mixture is stirred at room temperature for 56 hours while maintaining the pH between 5 and 6 by the addition of 1 N hydrochloric acid. The methanol is evaporated, the aqueous phase is alkalified to pH=14 with concentrated sodium hydroxide solution and then saturated with sodium chloride. The mixture is extracted with dichloromethane, the organic phase is dried over magnesium sulphate, filtered and then evaporated under reduced pressure to give 0.55 g of product.
Melting point: 104°-105° C.

The hydrochloride is prepared by addition of 25 ml of 0.1 N hydrochloric acid in 2-propanol. 0.65 g of product is obtained.
Melting point: 304°-307° C.

EXAMPLE 3

Compound No. 7

2-[4-[[3-(5-Fluoro-2-methoxyphenoxy)propyl]amino]piperidin-1-yl ] pyrimidine-4-carboxamide, hydrochloride 1.7 g (0.00768 mol) of 2-(4-aminopiperidin-1-yl)pyrimidine-4-carboxamide, 2.0 g (0.00768 mol) of 3-(5-fluoro-2-methoxyphenoxy)propylamine, 1.6 g (0.0115 mol) of potassium carbonate and 30 ml of N,N dimethylformamide are introduced under argon into a 100 ml, three-necked round bottom flask and the reaction mixture is brought to a temperature of 70° C. for 8 hours.

The mixture is poured onto a mixture of water and ice, extracted with ethyl acetate, the organic phase is washed with water, dried and concentrated under reduced pressure. A yellow oil is obtained and the hydrochloride is prepared by reaction of 1.7 g (0.0042 mol) of base and 42 ml of 0.1 N hydrochloric acid in 2-propanol. The solvent is evaporated under reduced pressure and the residue is recrystallised from ethanol.
1.3 g of compound are obtained.
Melting point: 230°-232.5° C.

EXAMPLE 4

Compound No. 14

2-[4-[[[2-[5-Methyl-2-(1-methylethyl)phenoxy]ethyl]amino]methyl]piperidin-1-yl]pyrimidine-4-carboxamide, hydrochloride 4.1. 1,1-Dimethylethyl
[[1-[4-(aminocarbonyl)pyrimidin-2-yl]piperidin-4-yl]methyl]carbamate 14 g (0.0653 mol) of 1,1-dimethylethyl [(piperidin-4-yl)methyl]carbamate, 10.45 g (0.0663 mol) of 2-chloropymiridine-4-carboxamide, 13.55 g (0.098 mol) of potassium carbonate, 0.3 g of sodium iodide and 330 ml of N,N-dimethylformamide are introduced into a 1 liter, three-necked round bottom flask. The mixture is stirred for 24 hours at room temperature and under argon atmosphere and is then poured into 500 ml of water. The mixture is extracted with dichloromethane, the organic phase is washed with water, dried over magnesium sulphate, filtered and the solvent evaporated under reduced pressure. The crude crystallised product is taken up with ethyl ether and 20.4 g of white solid are obtained.
Melting point: 172°-174.5° C.

4.2.
2-[4-(Aminomethyl)piperidin-1-yl]pyrimidine-4-carboxamide 20.3 g (0.0605 mol) of 1,1-dimethylethyl [[1-[4-(aminocarbonyl)pyrimidin-2-yl]piperidin-4-yl]methyl]-carbamate, 200 ml of dichloromethane and 200 ml of trifluoroacetic acid are introduced into a 1 liter round bottom flask and the mixture is heated at 40° C. for 4.5 hours.

The reaction mixture is diluted with 300 ml of dichloromethane, cooled to 0° C. and a flow of gaseous ammonia is passed through it. The insoluble material is removed by filtration, the solvent is evaporated under reduced pressure, the residue is taken up with dichloromethane, the solution is dried over magnesium sulphate, filtered and evaporated under reduced pressure. 13.8 g of crystallised deprotected amine are obtained, which is used as it is in the following stage.
Melting point: 144°-148° C.

4.3.
2-[4-[[[2-[5-Methyl-2-(1-methylethyl)phenoxy]ethyl]amino]methyl]piperidin-1-yl]pyrimidine-4-carboxamide, hydrochloride.

3 g (0.0128 mol) of 2-[4-(aminomethyl)piperidin-1-yl]pyrimidine-4-carboxamide, 3.3 g (0.0128 mol) of 2-[5-methyl- 2-(1-methylethyl)phenoxy]ethyl bromide and 2.65 g (0.0192 mol) of potassium carbonate are suspended, under argon, in 50 ml of N,N-dimethylformamide and the mixture is heated at 70° C. for 9 hours.

The mixture is cooled to room temperature, poured into 250 ml of water and extracted with ethyl acetate. The organic phase is washed with water, dried over magnesium sulphate, filtered and the solvent is evaporated under reduced pressure.

After purification by chromatography on silica (eluent: dichloromethane/methanol 96/4 to 90/10), 1.85 g of base are isolated.

To prepare the hydrochloride, the base is dissolved in 50 ml of methanol, 45 ml of 0.1 N hydrochloric acid in 2-propanol are added and the solvents are evaporated under reduced pressure. The evaporation residue is recrystallised from ethanol to give 1.4 g of compound.

Melting point: 197°-199.5° C.

EXAMPLE 5

Compound No. 13

2-[3-[[[2-(2-Methoxyphenoxy)ethyl]amino]methyl]-piperidin-1-yl]pyrimidine-4-carboxamide, hydrochloride

5.1. 1,1-Dimethylethyl [[1-[4-(aminocarbonyl)pyrimidin-2-yl]piperidin-3-yl]methyl]carbamate 10 g (0.0467 mol) of 1,1-dimethylethyl [(piperidin-3-yl)methyl]carbamate, 7.5 g (0.0476 mol) of 2-chloropyrimidine-4-carboxamide, 9.7 g (0.07 mol) of potassium carbonate, 0.3 g of sodium iodide and 230 ml of N,N-dimethylformamide are introduced into a 1 liter, three-necked round bottom flask. The mixture is stirred for 24 hours at room temperature, under argon atmosphere, and is then poured into 500 ml of water. The mixture is extracted with dichloromethane, the organic phase is washed with water, dried over magnesium sulphate, filtered and the solvent evaporated under reduced pressure. The crude crystalline product is taken up with petroleum ether and 15 g of white solid are obtained.

Melting point: 131°-135° C.

5.2. 2-[3-(Aminomethyl)piperidin-1-yl]pyrimidine-4-carboxamide 15 g (0.0447 mol) of 1,1-dimethylethyl [[1-[4(aminocarbonyl)pyrimidin-2-yl]piperidin-3-yl]methyl]carbamate, 150 ml of dichloromethane and 150 ml of trifluoroacetic acid are introduced into a 1 liter round bottom flask and the mixture is heated at 40° C. for 5 hours.

The mixture is diluted with 230 ml of dichloromethane, cooled to 0° C. and a flow of gaseous ammonia is passed through it. The insoluble material is removed by filtration, the solvent is evaporated under reduced pressure, the residue is taken up in dichloromethane, the solution is dried over magnesium sulphate, filtered and evaporated under reduced pressure.

10.2 g of amine are obtained in the form of a yellowish oil which is used as it is in the following stage.

5.3. 2-[3-[[[2-(2-Methoxyphenoxy)ethyl]amino]methyl]-piperidin-1-yl]pyrimidine-4-carboxamide, hydrochloride 3.5 g (0.0149 mol) of 2-[3-(aminomethyl)piperidin-1-yl]pyrimidine-4-carboxamide, 3.5 g (0.0151 mol) of 2-(2-methoxyphenoxy)ethyl bromide and 3.1 g (0.0224 mol) of potassium carbonate are suspended, under argon, in 60 ml of N,N-dimethylformamide and the mixture is heated at 70° C. for 12.5 hours.

The mixture is cooled to room temperature, poured into 250 ml of water and extracted with ethyl acetate. The organic phase is washed with water, dried over magnesium sulphate, filtered and the solvent is evaporated under reduced pressure.

After purification by chromatography on silica (eluent: dichloromethane/methanol 96/4 to 90/10), 1.7 g of base are isolated.

In order to prepare the hydrochloride, the base is dissolved in 30 ml of ethanol, 44 ml of 0.1 N hydrochloric acid in 2-propanol are added, the solvents are evaporated under reduced pressure and the residue is recrystallised from 2-propanol.

1.3 g of compound are finally obtained.

Melting point: 199°-201° C.

EXAMPLE 6

Compound No. 1

2-(4-Aminopiperidin-1-yl)pyrimidine-4-carboxamide, hydrochloride

6.1. 1,1-Dimethylethyl [1-[4-(aminocarbonyl)pyrimidin-2-yl]piperidin-4-yl]carbamate 7.7 g (0.0385 mol) of 1,1-dimethylethyl (piperidin-4-yl)carbamate, 6.15 g 0.039 mol) of 2-chloropyrimidine-4-carboxamide, 8 g (0.0578 mol) of potassium carbamate, 0.3 g of sodium iodide and 200 ml of N,N-dimethylformamide are introduced into a 500-ml, three-necked round bottom flask and the mixture is stirred for 24 hours at room temperature and under an argon atmosphere.

The mixture is poured into 500 ml of water, extracted with dichloromethane, the organic phase is washed with water, dried over magnesium sulphate, filtered and the solvent is evaporated under reduced pressure. The crude crystallised product is taken up with diethyl ether and 11.8 g of white solid are obtained.

Melting point: 216.5°-218° C.

6.2. 2-(4-Aminopiperidin-1-yl)pyrimidine-4-carboxamide, hydrochloride 13.9 g (0.0433 mol) of 1,1-dimethylethyl [1-[4-(aminocarbonyl)pyrimidin-2-yl]piperidin-4-yl]carbamate, 140 ml of dichloromethane and 140 ml of trifluoroacetic acid are introduced into a 1-liter, three-necked round bottom flask and the mixture is heated for 4 hours at 40° C.

The mixture is diluted with 300 ml of dichloromethane, cooled to 0° C. and a flow of gaseous ammonia is passed through it. The insoluble material is removed by filtration, the solvent is evaporated under reduced pressure, the residue is taken up with dichloromethane, the solution is dried over magnesium sulphate, filtered and the solvent is evaporated under reduced pressure. 8.3 g of crystallised deprotected amine are obtained.

Melting point: 105°-107.5° C.

The hydrochloride is prepared from this by means of 0.1 N hydrochloric acid in 2-propanol.

Melting point: 304°-307° C.

EXAMPLE 7

Compound No. 5

2-[4-[[2-(5-Fluoro-2-methoxyphenoxy)ethyl]amino]-piperidin-1-yl]pyrimidine-4-carboxamide, hydrochloride A suspension of 0.6 g (0.00271 mol) of 2-(4-aminopiperidin-1-yl)pyrimidine-4-carboxamide, 0.68 g (0.00271 mol) of 2-(5-fluoro-2-methoxyphenoxy)ethyl bromide and 0.56 g (0.00407 mol) of potassium carbonate in 10 ml of N,N-dimethylformamide is prepared, under an argon atmosphere, and the mixture is stirred at room temperature for 24 hours and then at 90° C. for 3.5 hours.

The mixture is cooled to room temperature, poured into 100 ml of water and extracted with ethyl acetate. The organic phase is washed with water, dried over magnesium sulphate, filtered and the solvent is evaporated under reduced pressure. The evaporation residue is purified by chromatography on a silica gel column by eluting with a mixture of 95/5 to 92/8 dichloromethane/methanol and 0.6 g of base is obtained.

In order to prepare the hydrochloride, the base is dissolved in 10 ml of methanol, 15.5 ml of 0.1 N hydrochloric acid in 2-propanol are added and the solvents are evaporated under reduced pressure. The residue is recrystallised from a mixture of ethanol and 2-propanol and 0.4 g of hydrochloride are finally obtained.

Melting point: 236°–237.5° C.

EXAMPLE 8

Compound No. 8

2-[4-[[3-(4-Fluorophenoxy)propyl]amino]piperidin-1-yl]pyrimidine-4-carboxamide, hydrochloride A suspension of 1.5 g (0.00678 mol) of 2-(4-aminopiperidin-1-yl)pyrimidine-4-carboxamide, 1.6 g (0.00678 mol) of 3-(4-fluorophenoxy)propyl bromide and 1.4 g (0.0102 mol) of potassium carbonate is prepared, under an argon atmosphere, in 25 ml of N,N-dimethylformamide and the mixture is heated at 70° C. for 7.5 hours.

The mixture is cooled to room temperature, poured into 250 ml of water and extracted with ethyl acetate. The organic phase is washed with water, dried over magnesium sulphate, filtered and the solvent evaporated under reduced pressure.

The residue is purified by chromatography on a silica gel column by eluting with a 95/5 to 90/10 dichloromethane/methanol mixture and 1.05 g of base are isolated.

In order to prepare the hydrochloride, the base is dissolved in 20 ml of methanol, 28 ml of 0.1 N hydrochloric acid in 2-propanol are added, the solvents are evaporated under reduced pressure and the residue is recrystallised from a mixture of methanol and ethanol.

0.6 g of hydrochloride is finally isolated.

Melting point: 243°–246° C.

The following Table illustrates the chemical structures and the physical properties of some compounds according to the invention.

TABLE

Structure (I): $R\text{-}N(R_1)\text{-}(CH_2)_q\text{-}[(CH_2)_p, (CH_2)_m]\text{-}N\text{-}$(pyrimidine)$\text{-}C(=O)NH_2$

| No. | R | X | n | m,p | q | $R_1$ | Salt | M.P. (°C.) |
|---|---|---|---|---|---|---|---|---|
| 1 | H | — | — | 1,1 | 0 | H | HCl | 304–307 |
| 2 | CH$_3$ | — | — | 1,1 | 0 | CH$_3$ | HCl | 270–272 |
| 3 | phenyl-O-(CH$_2$)$_m$– (X-substituted) | 2-OCH$_3$ | 2 | 1,1 | 0 | H | HCl | 231–233 |
| 4 | phenyl-O-(CH$_2$)$_m$– (X-substituted) | 2-OCH$_3$, 5-Cl | 2 | 1,1 | 0 | H | HCl | 226–229 |
| 5 | phenyl-O-(CH$_2$)$_m$– (X-substituted) | 2-OCH$_3$, 5-F | 2 | 1,1 | 0 | H | HCl | 236–237.5 |
| 6 | phenyl-O-(CH$_2$)$_m$– (X-substituted) | 4-F | 2 | 1,1 | 0 | H | HCl | 229–231 |
| 7 | phenyl-O-(CH$_2$)$_m$– (X-substituted) | 2-OCH$_3$, 5-F | 3 | 1,1 | 0 | H | HCl | 230–232.5 |

TABLE-continued (I) Structure: R(R₁)N-(CH₂)q-CH[(CH₂)p-]...(CH₂)m- linked to N of pyrimidine ring bearing C(=O)NH₂

| No. | R | X | n | m,p | q | R₁ | Salt | M.P. (°C.) |
|---|---|---|---|---|---|---|---|---|
| 8 | X-C₆H₄-O-(CH₂)ₘ- | 4-F | 3 | 1,1 | 0 | H | HCl | 243–246 |
| 9 | X-C₆H₄-O-(CH₂)ₘ- | 2-iC₃H₇, 5-CH₃ | 2 | 1,1 | 0 | H | HCl | 254–257 |
| 10 | X-C₆H₄-O-(CH₂)ₘ- | 4-F | 2 | 1,1 | 1 | H | HCl | 237–239 |
| 11 | X-C₆H₄-O-(CH₂)ₘ- | 4-F | 2 | 0,2 | 1 | H | HCl | 184–187 |
| 12 | X-C₆H₄-O-(CH₂)ₘ- | 2-OCH₃ | 2 | 1,1 | 1 | H | HCl | 183–185 |
| 13 | X-C₆H₄-O-(CH₂)ₘ- | 2-OCH₃ | 2 | 0,2 | 1 | H | HCl | 199–201 |
| 14 | X-C₆H₄-O-(CH₂)ₘ- | 2-iC₃H₇, 5-CH₃ | 2 | 1,1 | 1 | H | HCl | 197–199.5 |

Note: In column "X", "iC₃H₇" denotes a 1-methylethyl group; in column "Salt", "HCl" denotes a hydrochloride.

The compounds of the invention were made the subject of studies regarding their antagonist activity of $\alpha_1$-adrenergic receptors at the level of the lower urinary apparatus.

Their in vitro activity was studied on isolated rabbit urethra.

Adult rabbit urethra rings are prepared according to the method of Ueda et al., Eur. J. Pharmacol., (1984), 103, 249–254, and then, after sensitisation to noradrenalin, the concentration-response curve to phenylephrine is determined in the absence and in the presence of the study compound.

The potency of the $\alpha_1$-adrenergic antagonism of each compound is evaluated by calculation of the pA₂, the antilogarithm of the molar concentration of the antagonist in the presence of which the concentration of the agonist must be doubled to cause the same effect as in its absence.

The pA₂ values of the compounds are of the order of 5.5 to 9.

The in vivo activity of the compounds of the invention was studied with regard to their effect on the urethral hypertonia caused by the stimulation of the sympathetic fibers of the hypogastric nerve in anaesthetized cat.

Adult male cats are anaesthetized by sodium pentobarbital and they are prepared according to the method of Theobald, J Auton. Pharmac., (1983), 3, 235-239, in order to obtain a urethral hypertonia by stimulation of the sympathetic fibers of the hypogastric nerve. The contractile responses of the urethra to the electrical stimulation of the hypogastric nerve are recorded before and after intravenous administration of the study compounds, at cumulative doses from 1 to 1000 μg/kg.

The strength of the $\alpha_1$-adrenergic antagonism of each compound is evaluated by calculation of the $ID_{50}$, the dose which inhibits by 50% the urethral hypertonia.

The $ID_{50}$ values of the compounds of the invention are of the order of 0.01 to 1 mg/kg.

The results of the tests show that the compounds of the invention show, in vitro, an antagonist activity of the $\alpha_1$-adrenergic receptors of the smooth muscles of the lower urinary apparatus (urethra) stimulated by an $\alpha_1$-adrenergic agonist (phenylephrine). In vivo, they inhibit the urethral hypertonia caused by sympathetic nervous stimulation.

The compounds of the invention can thus be used for the symptomatic treatment of diseases and complaints which involve a hyperactivity of the $\alpha_1$-adrenergic system at the level of the lower urinary apparatus, and especially for the treatment of benign hypertrophia of the prostate, of dysuria and of pollakiuria. For this purpose they may be formulated as pharmaceutical compositions, in which they are the active ingredient. To that end, they can be introduced in all forms appropriate for enteral or parenteral administration, combined with pharmaceutical excipients, for example in the form of tablets, sugar- coated pills, gelatin capsules, capsules, drinkable or injectable solutions or suspensions, or suppositories, the charges being such as to allow a daily dose from 0.5 to 500 mg of active substance.

We claim:

1. A compound which is a carboxamide derivative of formula (I)

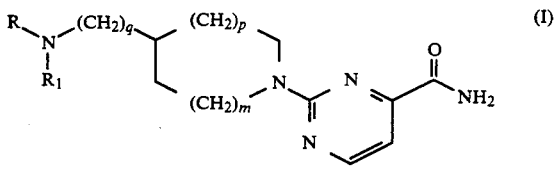

in which R represents a hydrogen atom, a methyl group or a phenoxyalkyl group of formula

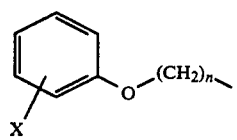

in which

X represents one or more substituents independently chosen from hydrogen, fluorine, chlorine, methyl, 1-methylethyl and methoxy and n is 2 or 3, m is 0 or 1 and p is 1 or 2 such that $m+p=2$, q is 0 or 1, and $R_1$ represents a hydrogen atom or a methyl group, or a pharmaceutically acceptable acid addition salt thereof.

2. A compound according to claim 1, which is in the form of a pure enantiomer or a mixture of enantiomers.

3. A compound according to claim 1, in which R represents a hydrogen atom, a methyl group or a phenoxyalkyl group of formula

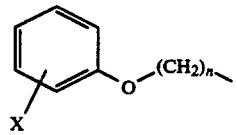

in which X represents one or more substituents independently chosen from fluorine, chlorine, methyl, 1-methylethyl and methoxy.

4. A compound according to claim 1, in which R represents a group of formula

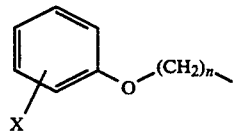

in which X is as defined in claim 1, n is 2, m is 1, p is 1 and q is 0.

5. A compound according to claim 1, in which the pharmaceutically acceptable acid addition salt is the hydrochloride.

6. A compound according to claim 1, which is:

2-[4-[[2-(2-methoxyphenoxy)ethyl]amino]piperidin-1-yl]pyrimidine-4-carboxamine or the hydrochloride thereof;

2-(4-aminopiperidin-1-yl)pyrimidine-4-carboxamide or the hydrochloride thereof;

2-[4-[[3-(5-fluoro-2-methoxyphenoxy)propyl]amino]-piperidin-1-yl]pyrimidine-4-carboxamide or the hydrochloride thereof;

2-[4-[[[2-[5-methyl-2-(1-methylethyl)phenoxy]ethyl]amino]-methyl]piperidin-1-yl]pyrimidine-4-carboxamide or the hydrochloride thereof;

2-[3-[[[2-(2-methoxyphenoxy)ethyl]amino]methyl]-piperidin-1-yl]pyrimidine-4-carboxamide or the hydrochloride thereof;

2-(4-aminopiperidin-1-yl)pyrimidine-4-carboxamide or the hydrochloride thereof;

2-[4-[[2-(5-fluoro-2-methoxyphenoxy)ethyl]amino]-piperidin-1-yl]pyrimidine-4-carboxamide or the hydrochloride thereof; or 2-[4-[[3-(4-fluorophenoxy)propyl]amino]piperidin-1-yl]pyrimidine-4-carboxamide or the hydrochloride thereof.

7. A pharmaceutical composition comprising a pharmaceutically acceptable carrier and an effective amount of a compound as claimed in claim 1 for treating disorders involving hyperactivity of the $\alpha_1$-adrenergic system in the lower urinary tract.

8. A method of treating disorders involving hyperactivity of the $\alpha_1$-adrenergic system in the lower urinary tract which comprises administering to a patient an effective amount of a compound as claimed in claim 1.

* * * * *